United States Patent [19]

Koll

[11] Patent Number: 5,152,281
[45] Date of Patent: Oct. 6, 1992

[54] MASSAGING DEVICE

[76] Inventor: Walter Koll, Schulstrasse 22, Bendorf/Rhein, Fed. Rep. of Germany, 5413

[21] Appl. No.: 709,977

[22] Filed: Jun. 4, 1991

[30] Foreign Application Priority Data

Jul. 11, 1990 [DE] Fed. Rep. of Germany ....... 9010455

[51] Int. Cl.$^5$ .......................................... A61H 15/00
[52] U.S. Cl. .................................................. 128/57
[58] Field of Search .................. 128/57, 59, 60, 61, 128/62 R, 62 A; 132/320, 129, 131, 112; 15/230.11, 27

[56] References Cited

U.S. PATENT DOCUMENTS

| | | | |
|---|---|---|---|
| 2,310,804 | 2/1943 | Morrison | 128/57 |
| 2,787,261 | 4/1957 | McDonald et al. | 128/57 X |
| 3,374,784 | 3/1968 | Brent et al. | 128/61 |
| 3,638,939 | 1/1972 | Langley | 128/57 X |
| 3,850,163 | 11/1974 | Andis, Sr. | 128/57 |
| 4,381,776 | 5/1983 | Avolio | 128/62 R |
| 4,550,718 | 11/1985 | Kaeser | 128/57 |
| 4,669,452 | 6/1987 | Osawa | 128/32 X |
| 4,688,556 | 8/1987 | Keller, Jr. | 128/57 |
| 4,883,047 | 11/1989 | Guitay | 128/57 |
| 4,989,585 | 2/1991 | Auker | 128/57 |
| 4,993,408 | 2/1991 | Schweisfarth | 128/57 |

FOREIGN PATENT DOCUMENTS

| | | |
|---|---|---|
| 0092449 | 10/1983 | European Pat. Off. . |
| 0282173 | 9/1988 | European Pat. Off. . |
| 0346942 | 12/1989 | European Pat. Off. . |
| 3016469 | 11/1981 | Fed. Rep. of Germany ........ 128/57 |
| 388531 | 6/1965 | Switzerland . |

Primary Examiner—Robert A. Hafer
Assistant Examiner—Brian E. Harlon
Attorney, Agent, or Firm—Wegner, Cantor, Mueller & Player

[57] ABSTRACT

In a masssaging device, a fork-shaped part is arranged on a handle so as to oscillate about a swivelling spindle. The fork-shaped part has a rolling-body is rotatably mounted. By virtue of the oscillating arrangement of the fork-shaped part, the rolling-body axis can tilt to a limited extent to both sides out of a position extending parallel to the handle. The rolling body has a plurality of disks which are arranged individually so as to be rotatable on the rolling-body axis and, on their circumferential surface, have a toothing which rolls over the skin to be massaged during the use of the massaging device.

7 Claims, 2 Drawing Sheets

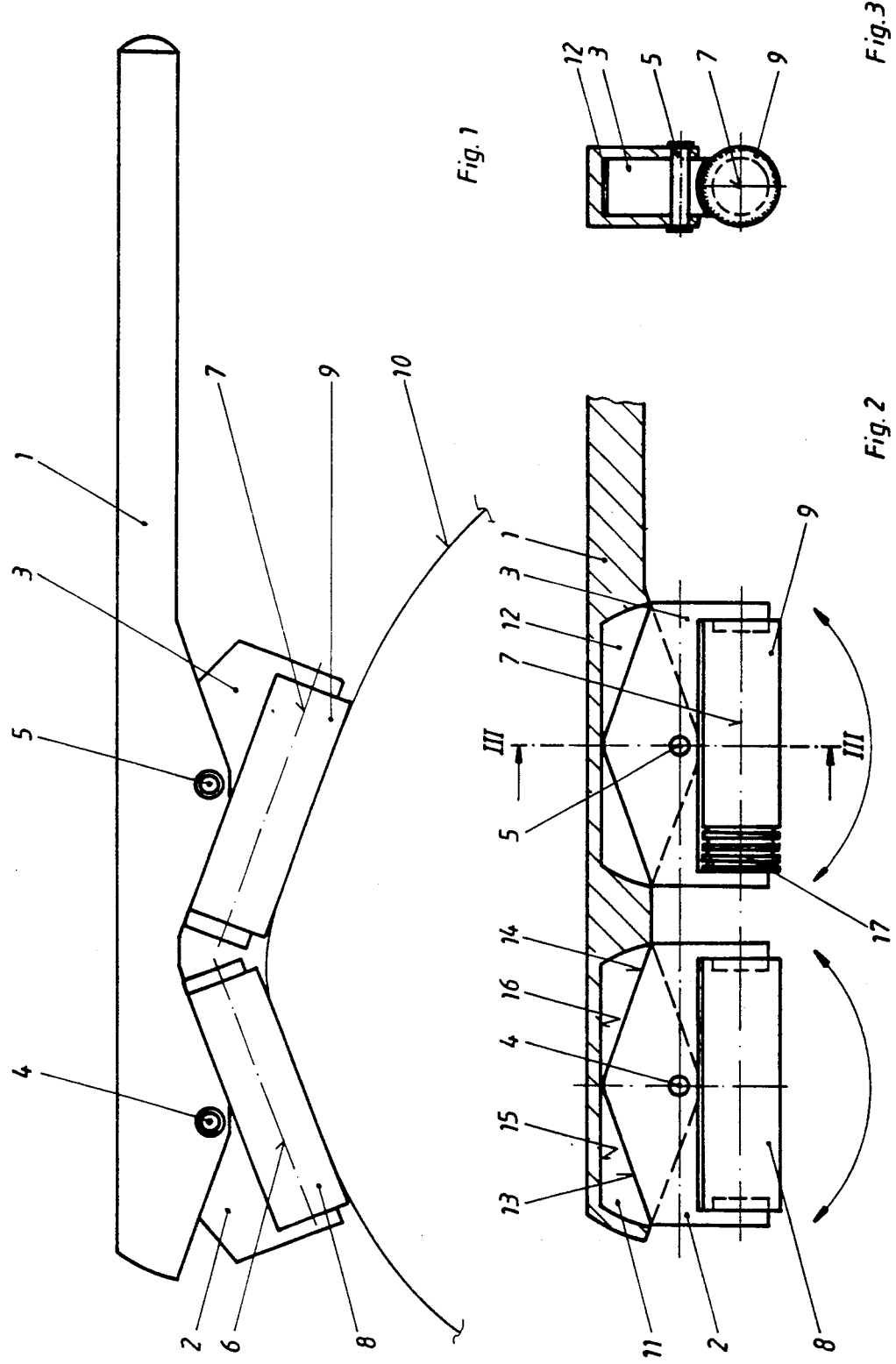

MASSAGING DEVICE

BACKGROUND OF THE INVENTION

This invention relates to a massaging device.

Massaging devices of the type which comprises a handle and at least one rolling body serving for the rolling massage, rotatably mounted on a rolling-body axis of the handle, in which the rolling-body axis is arranged in such a way as to be tiltable about a swivelling spindle extending transversely to the principal direction of extension of the handle, are described, for example, in European Patent 0 346 942. In the known massaging device, the swivelling axis of the rolling-body axis extends along the center line or in the midplane of the handle, between the handle and the rolling body. Since the rolling-body axis extends in the plane of the handle or in alignment with the handle, that end of the handle which is on the rolling-body side is only a short distance from the surface of the skin during massaging. As a result, there is the risk during use of the massaging device that that end of the handle which is on the swivelling-axis side will rub across the skin, giving rise to the possibility of injuries or at least being unpleasant.

A further disadvantage of the known massaging device consists in the fact that the rolling body is in a fixed angular position relative to the handle during massaging. It is therefore necessary, when rolling in the longitudinal direction over curved parts of the skin, to alter the angular position of the handle to ensure that the rolling body is in contact over as large an area as possible. This adaptation to the contours of the skin requires considerable skill and attention.

SUMMARY OF THE INVENTION

It is an object of the invention to further develop a massaging device of the type stated at the outset in such a way that it is simple and effective to use, even in the case of parts of the body which are highly curved, and does not pose the risk of injuring the skin.

This object is achieved according to the invention by virtue of the fact that the rolling-body axis is arranged to the side of the handle in a fork-shaped part connected swivellably to the handle by the swivelling spindle, and that the swivelling spindle extends centrally in the fork-shaped part and thus also centrally in relation to the rolling body.

By virtue of this design, the rolling body extends parallel to the longitudinal axis of the handle instead of in alignment with it. As a result, it is at a distance from the handle such that contact of the handle with the skin during massaging is excluded. By virtue of the central arrangement of the swivelling spindle, the rolling body is held in oscillating fashion on the handle. It therefore adapts during massaging to the contour of the parts of the skin to be massaged, even if the angular position of the handle is constant, thus guaranteeing as good a contact of the rolling body as possible. By virtue of the design in accordance with the innovation, the massaging device is very particularly suitable for treating the face since this has a large number of convexities and convacities, for example the eye sockets, the projecting cheek bones, the nose, the chin and the lip part. By virtue of the oscillating suspension of the rolling body, overstressing of projecting parts of the body is avoided even in the case of a prolonged massage.

The rolling body can be of widely varying design. It preferably comprises a plurality of individual disks which have a toothing on their outer curved surface, as described in French Patent 843,987. Instead of a toothing, the rolling body can also have needle-shaped points, as shown in German Offenlegungsschrift 32 21 750. The worm-like design of the rolling body shown in German Offenlegungsschrift 36 10 220 can also be employed in the present invention.

The design of the massaging device is particularly simple in terms of construction if the fork-shaped part is inserted into a recess, open towards one side, of the handle and the swivelling spindle is guided by two side parts of the handle, said side parts delimiting the recess.

In the massaging device according to the present invention, the swivellability of the fork-shaped part can be limited in a simple manner by stop faces of the fork-shaped part and contact faces within the recess.

It has proven particularly advantageous for the handling of the massaging device if the swivellability of the fork-shaped part is limited in such a way that in one end position the rolling body extends parallel to the handle and in its other end position forms an acute angle with that end of the handle which is on the rolling-body side.

For massaging curved parts of the skin it is advantageous if two fork-shaped parts each having a rolling body are arranged in alignment one behind the other in the handle. If such a massaging device is, for example, rolled in the longitudinal direction of the spinal column, one rolling body tilts to one side and the rolling body on the other side of the spinal column tilts to the other side, with the result that both rolling bodies rest against the skin over their full length.

The massaging device can optionally be used with a handle oriented parallel to the axis of the rolling bodies or with a handle oriented transversely to them if the fork-shaped parts are arranged in a carrier part and the handle is connected to the carrier part in such a way as to be swivellable about an axis extending perpendicularly to the rolling-body axis. As a result, the massaging device according to the invention can be used from case to case as a massaging device with the overall shape of a fork, described, for example, in French Patent 843,978.

It contributes to the further improvement of the handling of the massaging device if in addition to being connected to the carrier part in such a way as to be swivellable about the axis extending perpendicularly to the rolling-body axes, the handle is connected to said carrier part in such a way as to be swivellable about a spindle extending parallel to the rolling-body axes.

Massaging devices with rolling bodies arranged one behind the other are preferred in certain cases because with them it is possible to exercise an influence on a larger area of skin than in the case of a massaging device with only one rolling body or a plurality of rolling bodies next to one another. The principles of the invention can also be applied in the case of a so-called double roller by arranging two rolling bodies one behind the other in the carrier part.

In addition to the exercising of a mechanical influence on the skin, the massaging device can also act electrically on the skin if the rolling body is connected to a source of electric current. The electric current gives rise to a tingling feeling at the surface of the skin during massaging. The muscles and nerves are stimulated thereby.

An increase in the effect of the massage can also be achieved by connecting the rolling body to an electric vibrator.

The massaging device is independent of the current supply if a battery is arranged in the handle for the purpose of supplying said device with voltage.

The invention admits of numerous embodiments. Two of these are depicted in the attached drawing and are described below.

BRIEF DESCRIPTION OF THE DRAWINGS

FIG. 1 is a side elevational view of a massaging device according to the invention;

FIG. 2 is a side elevational view in longitudinal section through the massaging device of FIG. 1;

FIG. 3 is a cross-sectional view through the massaging device along the line III—III in FIG. 2;

DESCRIPTION OF THE PREFERRED EMBODIMENTS

Figure 4:
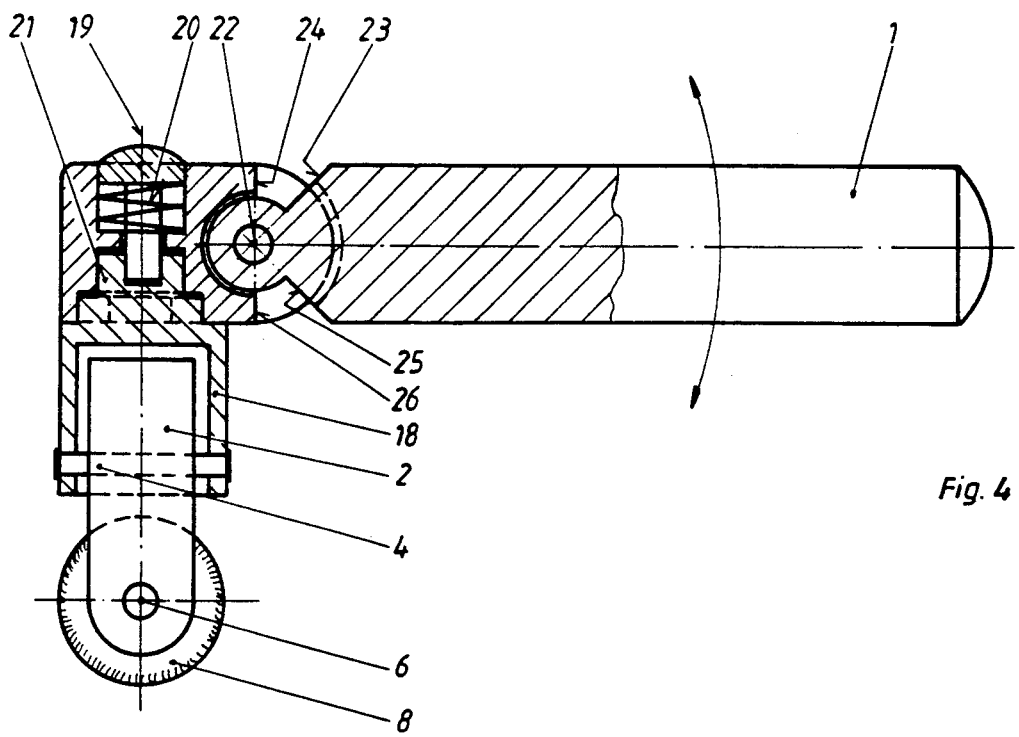
FIG. 4 is a side elevational view in, partly in cross-section through another embodiment of a massaging device according to the invention.

The massaging device depicted in FIG. 1 has a handle 1, in which two fork-shaped parts 2 and 3 are held so as to oscillate about swivelling spindles 4 and 5, respectively. Fork-shaped parts 2 and 3 support rolling bodies 8 and 9, respectively. Each of rolling bodies 8 and 9 is rotatable about a rolling-body axis 6 or 7. In the position depicted, these rolling bodies 8 and 9 are in contact with a convexly curved skin surface 10. They can be swivelled about the swivelling spindles 4 and 5 in such a way that they can move out of the position depicted, via an aligned position, into an obliquely oriented position.

From FIG. 2 it can be seen that two recesses 11 and 12 are present in the handle, each accommodating one fork-shaped part 2 or 3. Inside the respective recess 11 and 12, each of the fork-shaped parts 2 and 3 has two stop faces 13 and 14 which abut at an obtuse angle and, in the event of a swivelling movement of the fork-shaped parts 2 or 3, are capable of resting against contact faces 15 and 16, respectively, formed by the bottom of the recess 11 or 12. The swivellability of the fork-shaped parts 2 and 3 is limited thereby.

The rolling bodies 9 are represented in FIG. 2 by individual sketched disks 17, which can be rotatable about the rolling-body axis 7 and can be toothed on their circumferential surface, as described, for example, in French Patent 843,978.

FIG. 3 provides additional clarification of the design of the massaging device. The fork-shaped part 3 which is held in the recess 12 so as to oscillate about the swivelling spindle 5 can be seen. At least at the end in which the fork-shaped parts are disposed, the handle 1 is hollow, having a top and two opposed side walls, but is open at the bottom. The rolling body 9 rotatable about the rolling-body axis 7 is also depicted.

In the embodiment according to FIG. 4, the fork-shaped part 2 depicted is not held directly in a handle 1, but in a carrier part 18, so as to oscillate about the swivelling spindle 4. The handle 1 is connected to this carrier part 18 in such a way as to be adjustable about a vertical axis 19. In the position illustrated, a compression spring 20 holds the handle 1 in a toothing 21 of the carrier part 18. If the handle 1 is pulled upwards relative to the carrier part 18, counter to the force of the compression spring 20, the toothing 21 disengages. As a result, the handle 1 can be rotated by 90° and then locked again by releasing it. The compression spring 20 then presses it into the toothing 21 again.

It can furthermore be discerned from FIG. 4 that the handle 1 can, in addition, be swivelled about a spindle 22 extending transversely to the axis 19. This swivellability is limited on both sides by stop faces 23 and 24, on one side, and 25 and 26, on the other.

Figure 5:
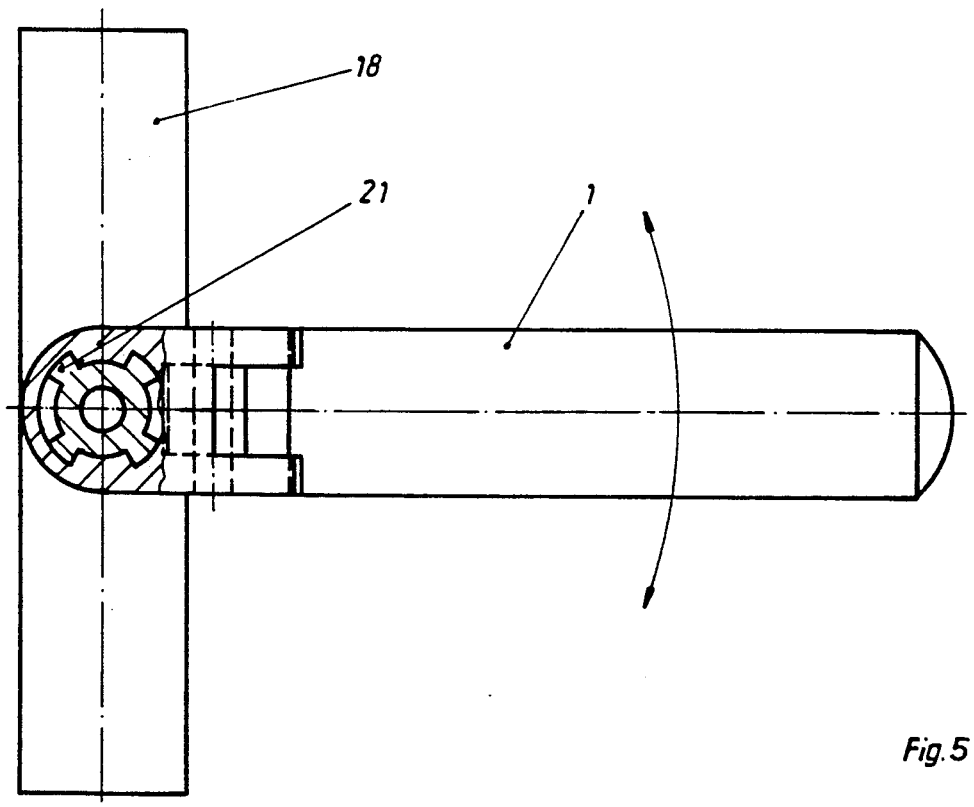
FIG. 5 is a plan view, partly in cross-section, of the massaging device according to FIG. 5.

The plan view, represented in partial section, in accordance with FIG. 5 shows the toothing 21 of the carrier part 18 by which the handle 1 can be fixed in the position extending transversely to the carrier part 18 and in a position in alignment with the latter. The horizontally extending spindle 22 which makes possible the additional swivellability of the handle 1 can also be seen.

While there is shown and described presently preferred embodiments of the invention, it is to be distinctly understood that the invention is not limited thereto, but may be otherwise variously embodied and practiced within the scope of the following claims.

What is claimed is:

1. A massaging device comprising:
   an elongated handle;
   a fork-shaped holder means connected to said handle at one end thereof so as to swivel about a swivelling axis extending transversely to said handle; and
   a rolling body for providing a rolling massage rotatably mounted in said fork-shaped holder means along a rolling-body axis, wherein the rolling-body axis is tiltable about said swivelling axis and the rolling-body axis is offset from the handle, said swivelling axis extending centrally in the fork-shaped holder means and also centrally in relation to the rolling body,
   wherein the fork-shaped holder means comprises a pair of angled stop faces and the handle comprises a corresponding pair of cooperating contact faces, whereby the ability of the fork-shaped holder means to swivel about the swivelling axis is limited by the stop faces contacting the corresponding contact faces of the handle.

2. A massaging device as claimed in claim 1, wherein the fork-shaped holder means is inserted into a recess, open towards one side, of the handle, and the swivelling axis passes through two side parts of the handle, said side parts delimiting the recess, wherein the corresponding cooperating contact faces are located in said recess.

3. A massaging device as claimed in claim 1, wherein the ability of the fork-shaped holder means to swivel is limited such that when a first angled stop face contacts its corresponding contact face, the rolling body axis extends parallel to the handle, and when the second angled stop face contacts its corresponding contact face, the rolling body axis forms an acute angle with the end of the handle to which the fork-shaped holder means is connected.

4. A massaging device as claimed in claim 1 comprising first and second fork-shaped holder means each of which are connected to said handle about a swivelling axis extending transversely to said handle, wherein a first rolling body is rotatably mounted in said first fork-shaped holder means along a first rolling-body axis and a second rolling body is rotatably mounted in said second fork-shaped holder means along a second rolling-body axis, said first and second fork-shaped holder means arranged such that the first and second rolling-body axes lie in a common plane.

5. A massaging device comprising:
an elongated handle;
a carrier means connected to an end of said handle;
at least one fork-shaped holder means connected to said carrier means so as to swivel about a swivelling axis extending transversely to said carrier means; and
a rolling body for providing a rolling massage rotatably mounted in said fork-shaped holder means along a rolling-body axis, wherein the rolling-body axis is tiltable about said swivelling axis and the rolling-body axis is offset from the handle, said swivelling axis extending centrally in the fork-shaped holder means and also centrally in relation to the rolling body;
wherein the handle is rotatable in relation to the carrier means and the fork-shaped holder means and the rolling body attached thereto about a rotational axis extending perpendicularly to the rolling body axis
said handle comprises two portions, a first portion connected to the carrier means at said rotational axis and a second part connected to said first part through a spindle means extending parallel to the rolling-body axis such that said second portion swivels about said spindle means in relation to the first portion;
wherein said first portion of the handle comprises a pair of angled stop faces and the second portion comprises a corresponding pair of cooperating contact faces, whereby the ability of the first portion to swivel about the spindle means is limited by the stop faces contacting the corresponding contact faces.

6. A massaging device as claimed in claim 5, further comprising means for releasably locking the handle at fixed increments around said rotational axis.

7. A massaging device as claimed in claim 5, comprising first and second fork-shaped holder means each of which are connected to said carrier means about a swivelling axis extending transversely to said handle, wherein a first rolling body is rotatably mounted in said first fork-shaped holder means along a first rolling-body axis and a second rolling body is rotatably mounted in said second fork-shaped holder means along a second rolling-body axis, said first and second fork-shaped holder means arranged such that the first and second rolling-body axes lie in a common plane.

* * * * *